United States Patent [19]

Lehmann

[11] Patent Number: 4,567,889
[45] Date of Patent: Feb. 4, 1986

[54] PROTECTIVE BREATHING AID DEVICE FOR DIVING OR OTHER OPERATION UNDER PRESSURE

[75] Inventor: Klaus Lehmann, Karlsdorf-Neuthard, Fed. Rep. of Germany

[73] Assignee: Interspiro GmbH, Forst, Fed. Rep. of Germany

[21] Appl. No.: 518,355

[22] Filed: Jul. 29, 1983

[30] Foreign Application Priority Data

Aug. 5, 1982 [DE] Fed. Rep. of Germany ....... 3229240

[51] Int. Cl.$^4$ ............................................. A62B 7/04
[52] U.S. Cl. ......................... 128/204.28; 128/205.16; 128/205.12; 128/205.24
[58] Field of Search ....................... 128/204.28, 205.16, 128/205.17, 205.13, 205.12, 205.24

[56] References Cited

U.S. PATENT DOCUMENTS

| | | | |
|---|---|---|---|
| 3,805,780 | 4/1974 | Cramer et al. | 128/205.26 |
| 4,224,940 | 9/1980 | Monnier | 128/205.16 |
| 4,364,384 | 12/1982 | Warncke et al. | 128/204.28 |

*Primary Examiner*—Henry J. Recla
*Attorney, Agent, or Firm*—Frishauf, Holtz, Goodman & Woodward

[57] ABSTRACT

A protective exhaling device of the circulating path type with exhaling protection, with its exhaling duct connected, in the circulating path through a $CO_2$ absorber and a gas volume equalizing chamber containing a variable volume of gas, to an inhaling duct to which there is connected a reservoir of compressed gas supplying oxygen for breathing, has a cylinder and piston unit connected to the pressure bottle pressure or to an intermediate regulator pressure for pneumatically producing a force applied to the variable volume chamber. That assures that the force determining the overpressure level is always exerted at the same magnitude independently of the amplitude of the content of the equalizing chamber of variable volume. There is an automatic switchover from overpressure operation to normal underpressure operation in the case of a major leakage. For this purpose the cylinder and piston unit is provided with an outlet valve that opens when the piston goes beyond a predetermined stroke position, so that the overpressure diminishes through the piston and at the same time the supply of pressurized gas is blocked. Thus, in the case of major leakage there is no risk that the compressed gas supply will empty quickly without the user of the apparatus noticing it. After elimination of the leak overpressure can be reinstated manually or automatically. The equipment is suitable both for diving and for compressed air breathing protection equipment generally.

12 Claims, 6 Drawing Figures

PROTECTIVE BREATHING AID DEVICE FOR DIVING OR OTHER OPERATION UNDER PRESSURE

The invention concerns a protective exhaling device of the circulating path type with exhaling protection, the exhaling duct being connected in the circulating path through a $CO_2$-absorber and a gas volume equalizing chamber containing a variable volume of gas, to an inhaling duct to which there is connected by at least one line a reservoir of compressed gas supplying oxygen for breathing, the chamber of variable volume being subjected to a force tending to reduce the volume of the chamber in order to establish a desired overpressure of gas in the circulation path. The invention is suitable both for diving equipment and for compressed air breathing protection equipment. Known types of such protective breathing aid devices provide for exertion of the force necessary for the desired overpressure in the circulation system by means of springs that bear directly, or through levers, on the variable volume chamber (compare, for example, published German patent application (OS) No. 30 23 747 and French patent No. 13 36 301).

These known devices have the disadvantage that the overpressure in the breathing loop decreases upon inhaling and increases with exhaling. This is because the springs serving to produce the overpressure relax during inhaling and build up force during exhaling. From the function technology point of view, for example in the case of a deep and heavy drawing of breath, the pressure regulating characteristic should operate with uniformity or with increase of pressure, since the resistance in the inhaling line increases with greater drawing off of gas and underpressure could arise in the mask or in the mouthpiece of the equipment.

SUMMARY OF THE INVENTION

It is an object of the present invention to improve the known protective breathing aid devices so that during inhaling the overpressure increases or at least remains constant, whereas with exhaling the overpressure decreases or at least remains constant. The pressure characteristic of the apparatus would therefore be fitted to the optimum conditions for respiratory physiology. The invention has the further object to improve the control of the overpressure, particularly automatic switching over from overpressure operation to normal or under pressure operation when a high loss of gas takes place through leakage or by removal of the protective mask and switching back automatically to overpressure operation when the escape of gas has been eliminated.

The first object of the invention is accomplished when the force applied to the variable volume chamber is pneumatically produced by a cylinder-and-piston unit connected to the pressure bottle pressure or to an intermediate regulated pressure, rather than by springs or the like. That assures that the force determining the overpressure level is always exerted at the same magnitude independently of the amplitude of the content of the equalizing chamber of variable volume. The pressure lowering heretofore occurring during inhaling and pressure rise during exhaling which in each case would be noticeable by increased resistance to breathing, is thus no longer to be feared. Particularly good conditions are provided when a pivoted lever is interposed between the cylinder-and-piston unit and the variable volume chamber, the configuration of the lever regarding lever arm length and the angle at which it bears being so selected that the force applied to the variable volume chamber increases with its emptying and decreases with its filling. In that way, during emptying, thus by inhaling, a pressure rise takes place and in filling, thus with exhaling, a pressure drop occurs. These pressure changes in each case operate in the direction desired on the basis of respiratory physiology: they compensate the pressure losses in the gas flow that are higher with reference to the static conditions.

The second object, namely the automatic switchover from overpressure operation to normal or underpressure operation in the case of a major leakage, is attained by providing the cylinder-and-piston unit with an outlet valve that opens when the piston goes beyond a predetermined stroke position, so that the overpressure diminishes through the piston and at the same time the supply of pressurized gas is blocked. The background for this automatic switching off of overpressure is that in the case of major leakage there is the risk that the compressed gas supply will empty quickly—without the user of the apparatus noticing it—and that the latter will then no longer be able to escape the danger.

It is already known from DE-OS No. 30 15 759 to provide automatic turning off of the oxygen supply. If this switch-off takes place at an instant in which the user of the apparatus is not capable of doing anything to the apparatus or after he has just exhaled, he can no longer inhale, because the variable volume chamber (breathing sac) is no longer in a position for providing gas to breathe. Even when after an exhaling event the oxygen supply is again released, a greater gas loss takes place until the next shut-off which will be repeated with every breath drawn so long as the user of the apparatus cannot terminate the leakage. Furthermore, the oxygen enrichment on account of the leakage raises the danger of explosion in a combustible atmosphere when such an atmosphere is present.

These disadvantages are avoided by the present invention. In the case of a leak the equipment is automatically switched over to normal operation. With the present invention it can thus not happen that the useful life of the apparatus is drastically reduced on account of a leak and that the person carrying it no longer has sufficient time to get out of the exhausted atmosphere of the system. After elimination of the leak overpressure can be reinstated manually or automatically.

It is advantageous for the cylinder-and-piston unit to be provided with an inlet valve for the pressurized gas against which the pressure in the cylinder urges opening of the valve while pressure in the supply line urges the valve to close. In that manner falling pressure in the cylinder on account of a leak automatically leads to closing of the inlet valve.

It is particularly useful for the cylinder-and-piston unit to have two pressure chambers, in one of which the piston and the outlet valve are located and in the other of which the inlet valve is mounted and for a partition wall between the chambers to have a central valve opening opened or closed by the inlet valve. The latter may have an extension passing through the opening in the partition wall for automatically switching in the overpressure.

In order to hold the inlet valve in its open position, there are several construction possibilities. On a mechanical basis the inlet valve can be held in its open position by an interlock which is arranged to be released out of that position by the piston rod when the piston passes beyond a predetermined stroke position, for example by having the piston rod run up against the interlock at a certain stroke stage and pushing the interlock element out of the position in which it blocks the inlet valve in its open position. Instead of that mechanical arrangement the inlet valve can be pneumatically held in its open position or released therefrom by the appropriate dimensioning of the surfaces opposed to effective pressures.

In order that the switchover to normal operation from overpressure operation should take place as fast as possible when there is a leak, it is desirable to provide the outlet valve in the form of an axially displaceable push-rod in a bore or tubular interior of the piston of the cylinder-and piston unit, the push-rod cooperating with a valve seat in the piston bore. Air passing through the valve flows around the push-rod and against a radially extending flange holding the valve open. The flange or impact plate leaves only a narrow annular gap between itself and the outer end of the piston rod when the push-rod lies against the valve seat.

The advantages described above are not only available for diving equipment but also for compressed air breath-protective equipment, in which case the force exerted for raising the pressure in the circulation path of the system is not exerted on a variable volume chamber used to equalize the volume of air in the user's lungs, but rather on the bellows or membrane of the compressed air breath-protection apparatus. This makes available the advantageous possibility for such compressed air breath protection apparatus which have an inhaling valve closing with the supply pressure, the valve being operatively connected in a known way with a control rod or lever to the bellows or membrane, for both the inhaling valve and also the cylinder-and-piston unit to be directly connected to the compressed gas tank or bottle. The forces on the bellows or membrane are then automatically equalized by the pneumatic overpressure control in the cylinder-and-piston unit. That means that it is possible to omit the previously necessary pressure reducer.

Finally, it is within the scope of the invention, for the case of protective breathing aid devices where the point of view of respiratory physiology is predominant and less depends upon the automatic switchover of overpressure to underpressure operation, to utilize the spring elements which are as such known for producing the force that generates the pressre increase, instead of the cylinder-and-piston unit, in such a way that the spring element bears against the variable volume chamber, bellows or membrane through a pivoted lever of such a design geometry regarding the effective lever arm lengths and their angle of application, that the force increases during inhaling, i.e. during emptying of the variable volume chamber or equivalent displacement of a membrane, whereas it decreases during exhaling, which is to say during filling of the variable volume chamber or equivalent displacement of a membrane.

BRIEF DESCRIPTION OF THE DRAWINGS

The invention is further described by way of illustrative examples with reference to the annexed drawings, in which.

DESCRIPTION OF THE PREFERRED EMBODIMENTS

Figure 1:
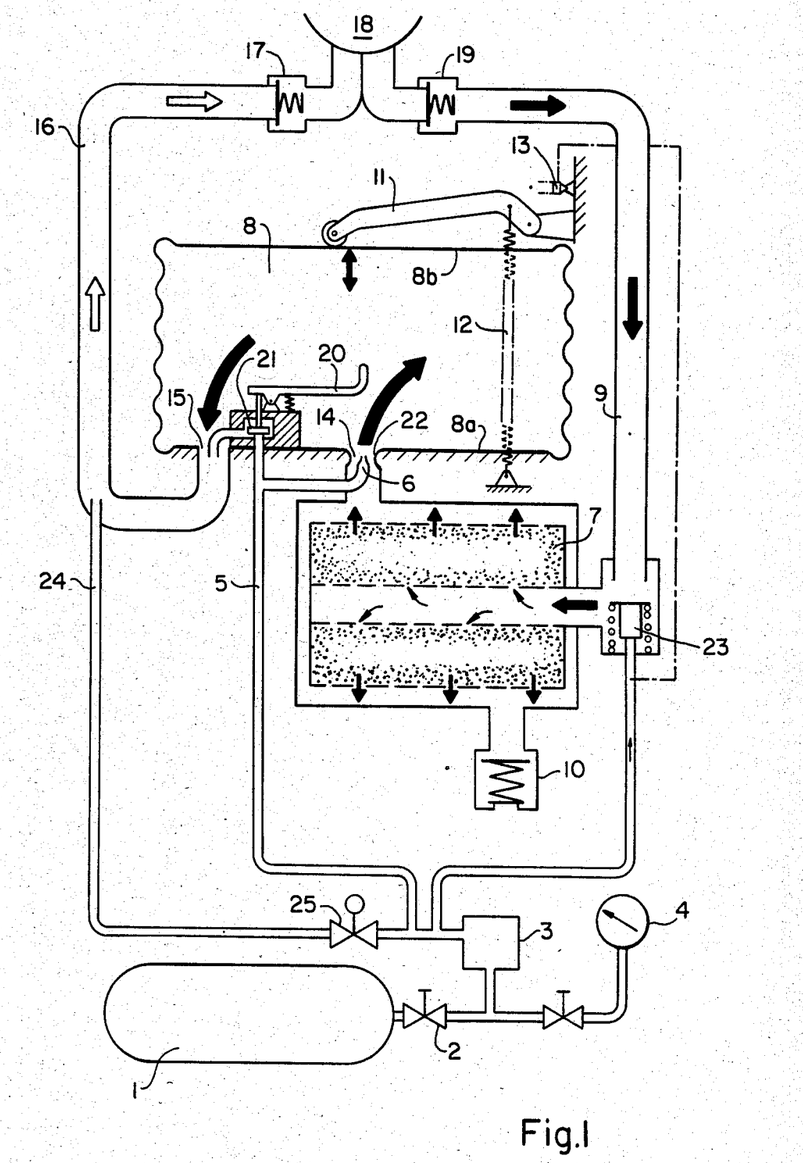
FIG. 1 is a schematic representation of the breathing gas circulation system in an embodiment in which the variable volume gas chamber has pressure applied to it over a lever.

As shown in FIG. 1, a pressure gas tank 1 filled with almost pure oxygen is connected through, in sequence, to a shut-off valve 2, a pressure-reducing valve 3, and a manometer 4. The pressure-reducing valve 3 reduces the pressure reigning in the gas tank 1 to the usual intermediate pressure and holds the latter approximately constant independently of the tank pressure. The oxygen flows continuously from the pressure-reducing valve 3, over a line 5 and a nozzle 6 into the breathing loop (circulation path).

In the illustrated example the nozzle 6 is located in the connection piece between the carbon dioxide absorber 7 and the gas volume equalization variable-volume chamber 8.

The $CO_2$-absorber is filled in the usual way with an alkaline powder or a similar compound having affinity for $CO_2$, which removes the $CO_2$ from the exhaled air which is supplied to the $CO_2$ absorber over the line 9. An overpressure valve 10 operates as soon as the permissible pressure in the breathing loop is overstepped. At the same time the valve 10 serves to blow off condensate separated from the breathed air.

The variable volume equalizing chamber 8 is constituted as a folded bellows having a fixed lower end wall 8a while its upper end wall 8b, although sufficiently rigid, is axially displaceable, so that it can execute the equalization movements during breathing in and out. This chamber is subjected to the effect of a lever 11 pivoted to a fixed point at one end and pressed by a tension spring 12 to apply a roller carried on its free end against the equalizing variable volume chamber 8. The spring force decreases by downwards swinging of the lever by the bent over end near the pivot, but because of the increasing effective lever arm,/the application force produced by the spring 12 practically always provides the same overpressure in the variable volume chamber 8.

Dot-dash lines in the upper right portion of FIG. 1 indicate that the force applied by the lever 11 can be generated not only through a spring 12, but instead or supplementarily also by a cylinder-and-piston unit 13 that is supplied with energy from the intermediate pressure established behind the pressure-reducing valve 3. The piston can be made to apply force on the chamber 8 in the manner illustrated in FIG. 3 and FIG. 5 (lever 52), for example.

While the entrance of the regenerated breathing gas takes place through the opening 14 into the variable volume container 8, a separate opening 15 is provided for outlet. This opening 15 is connected over the inhaling line 16 and the usual check valve 17 with the mask or mouthpiece 18 of the user. From that mask or mouthpiece the exhaled air flows through the check valve 19 into the exhaling line 9 and from there further into the $CO_2$-absorber 7, the loop thus being complete. Operation is as follows. Under normal operating conditions the oxygen fed into the breathing loop through the line 5 and the nozzle 6 is sufficient to compensate for the consumption of oxygen by the user and gas loss through the $CO_2$ absorber. The desired overpressure in the loop is maintained by the force applied by the spring 12 or by the cylinder-and-piston unit 13. The latter new elements press the lever 11 and thereby the upper end wall 8b of the equalizing variable volume chamber 8 downwards and thus produce a certain rise in pressure which is shared by the entire loop.

During breathing in and out the upper end wall 8b of the equalizing variable volume chamber executes a reciprocating movement. The overpressure in the variable container 8b, however, remains constant during that movement.

When the average oxygen requirement of the user is high, the oxygen quantity delivered through the nozzle 6 is no longer sufficient, the volume stored in the variable volume container 8 is therefore smaller, i.e., the upper end wall 8b wanders ever farther downwards during its reciprocating movements, until it comes to bear against an actuating lever 20 of an inhaling valve 21. This inhale valve 21 is also connected to the line 5. In the illustrated case it is built into the equalizing variable volume container 8, but it can also be located outside the container. What is important is that the actuating lever 20 of the inhaling valve should come against the end wall 8b or a correspondingly moving part of the equalizing variable volume container. It must merely be assured that beginning with a prescribed minimum remainder volume of the variable volume container 8 the inhaling valve 21 will be opened so that the oxygen supply will be matched to the increased requirement of the user. As soon as enough oxygen has flowed through the inhaling valve 21 for the upper end wall 8b to be moved upwards and to release the actuating lever 20, the inlet valve 20 closes again. The maintenance of the desired overpressure in the equalizing variable volume container 8 is not affected by this operation.

Of course, the overpressure valve 10, but not the two check valves 17 and 19, needs to be adjusted to the higher pressure conditions in the loop.

FIG. 1 further shows that the constant oxygen supply is delivered through the nozzle 6 axially into a venturi tube 22. In consequence the oxygen flowing in entrains with it the regenerated exhaled air coming from the $CO_2$-absorber, into the equalizing variable volume container i.e., the exhaling resistance is reduced. Finally, FIG. 1 shows also a few details of a known kind, for example a warning device 23 which raises the resistance to exhaling and produces a whistling sound when the oxygen bottle is not open or its contents are nearing exhaustion. Another connection line 24 between the pressure-reducing valve 3 and the inhaling line 16 allows flushing the entire loop with oxygen by means of a hand valve 25, which is of importance, especially at the beginning of use of the device.

Figure 2:
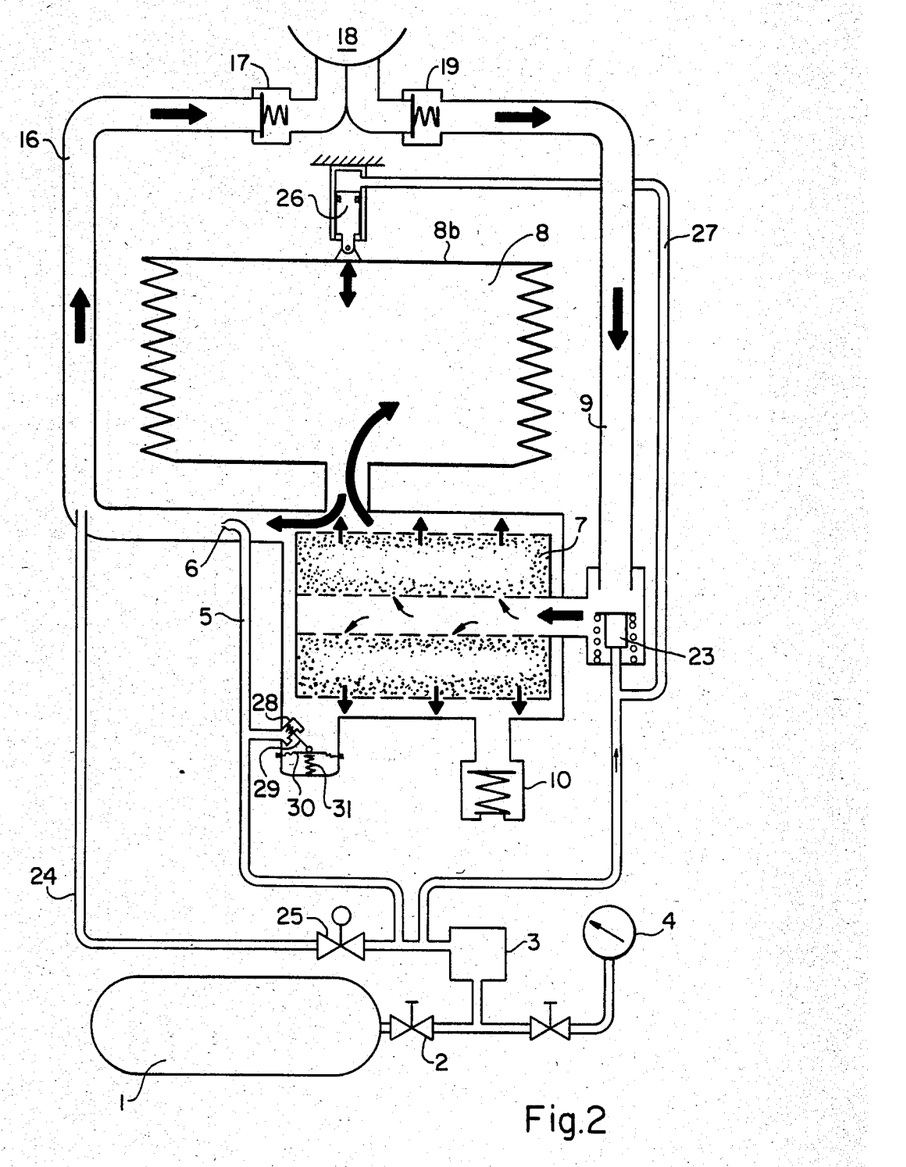
FIG. 2 is a schematic representation of a breathing gas circulation system in which a cylinder-and-piston unit is connected directly to a wall of the variable volume chamber.

FIG. 2 shows a breathing loop which, in principle, is of the same kind as that of FIG. 1. Corresponding parts are accordingly designated with the same reference numerals.

In distinction from FIG. 1, the equalizing variable volume container 8 is not subjected to force applied by a pivoted lever, but is subjected instead to the desired pressing force directly by a cylinder and piston unit 26. The latter is disposed centrally above the upper end wall 8b of the variable volume chamber and is supported for exertion of force by a fixed structural part. A line 27 connected to the intermediate pressure of the system provides the pneumatic connection for the cylinder and piston unit. The constant intermediate pressure behind the pressure reduction valve 3 which is independent of the pressure in the oxygen tank, here provides for the force independent of volume operating on the variable volume container 8 in the sense which tends to reduce its volume.

For reasons of convenience of illustration, the cylinder and piston unit 26 is shown on a much smaller scale in FIG. 2. In reality, it must permit a stroke which corresponds to the amplitude of the reciprocating movement of the upper end wall 8b of the variable volume chamber.

Furthermore, as a matter of distinction from FIG. 1, the inhaling valve 20 for increased oxygen requirement is provided in this case without dependence upon the stroke of the equalizing variable volume container 8, but rather constituted to be dependent on the pressure. For this purpose, the valve shaft 29 bears against a membrane 30, of which the surface is dimensioned in such a way relative to the remaining forces operating on the valve, that when a certain predetermined overpressure in the loop is understepped, the membrane 30 is pressed upward by the spring 31 and the valve opens.

In both of the above-described embodiments, it is assured that the overpressure in the system is not reduced by inhaling and is not increased by exhaling. In addition, in the arrangement of FIG. 1, a pressure increase in the inhaling phase and a pressure decrease in the exhaling case can be produced by corresponding dimensioning of the effective lever arms and their angle of attack. This principle can similarly be put into effect in the case of compressed air breathing protection devices. The lever 11 or the cylinder and piston unit 26 then bears against the membrane usually used in such apparatus, in such a way that the membrane is loaded in the sense of acting towards an opening of the inhaling valve with which it is connected.

Figures 3, 4:
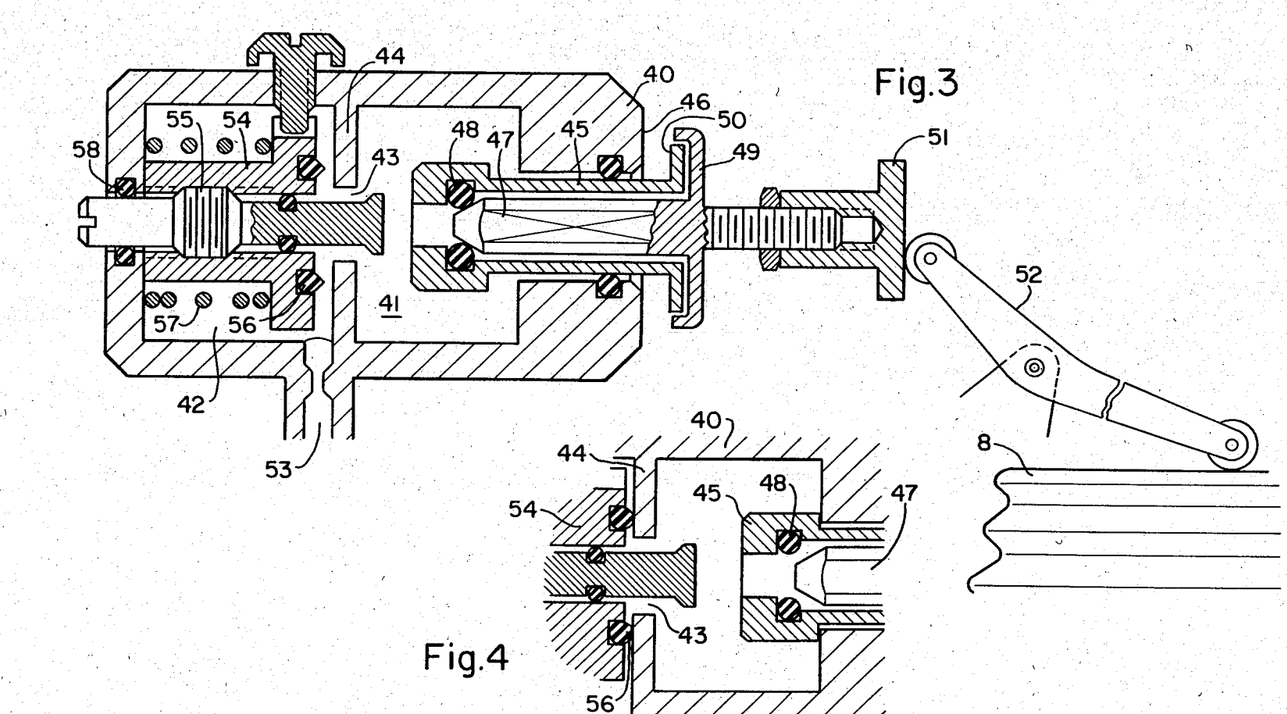
FIG. 3 is a cross-section of a cylinder-and-piston unit for use in a device of the invention, on a larger scale, shown in overpressure operation of the device.
FIG. 4 is a detail, also in section, of the cylinder-and-piston unit of FIG. 3, shown in underpressure operation.
Figures 5, 6:
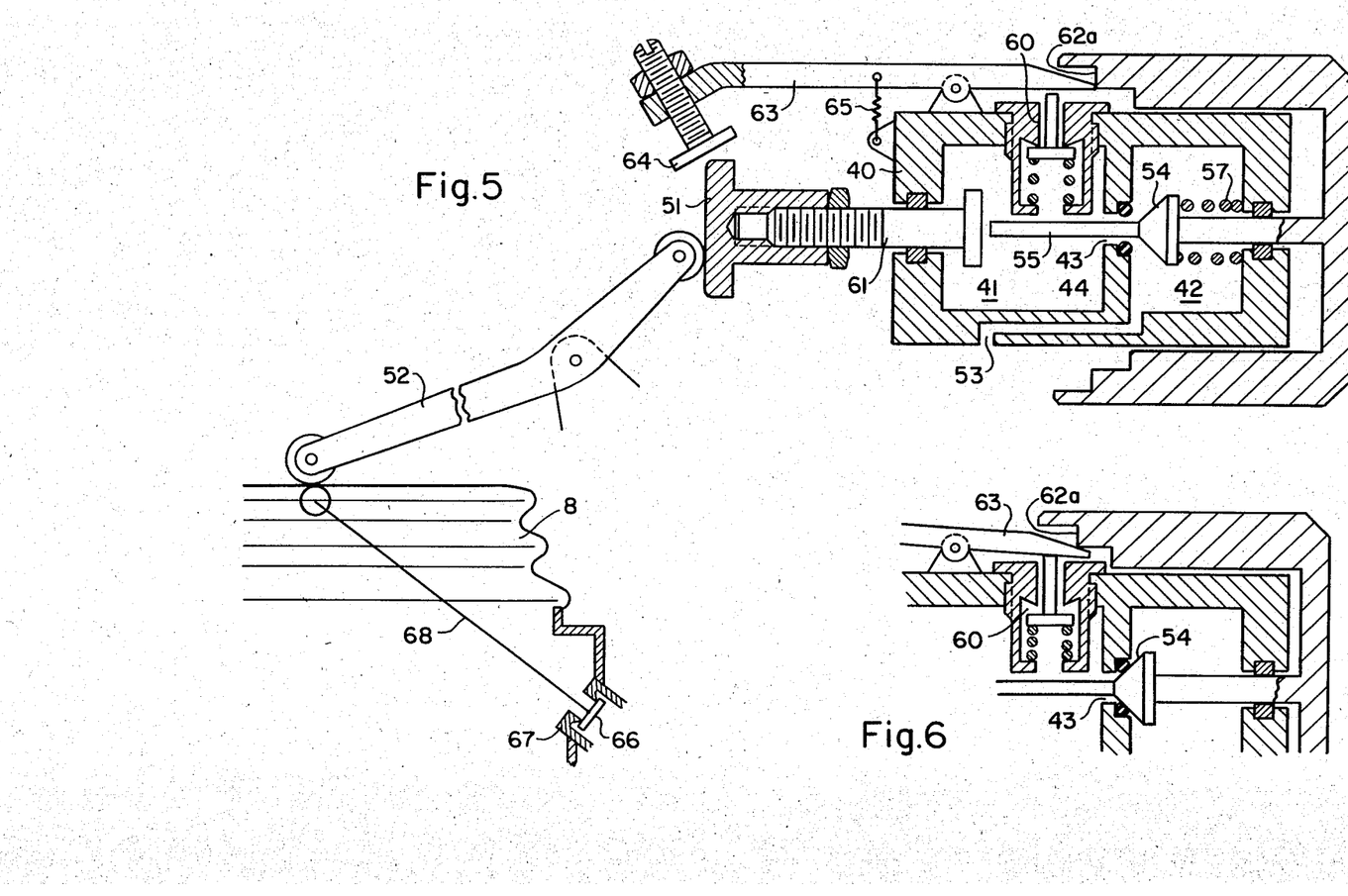
FIG. 5 is a section of a second embodiment of cylinder-and-piston unit, similar to FIG. 3 but having mechanical switch-off of overpressure operation.
FIG. 6 is a detail, also in section, of the cylinder-and-piston unit of FIG. 5, shown in underpressure operation.

FIGS. 3 and 4 show one and FIGS. 5 and 6 show another of cylinder and piston units incorporating a feature by which in the case of leakage and therefore in the case of any impermissibly high gas losses the over pressure will be automatically shut off.

The cylinder and piston unit according to FIGS. 3 and 4 consists of a cylinder 40 that contains two pressure chambers 41 and 42. The latter communicate with each other through a central bore in the partition wall 44. In the riqht-hand pressure chamber 41 there is a piston 45 constituted as a hollow piston. Its piston rod, of a diameter somewhat reduced from that of the piston head runs through a seal collar 46. Inside of the piston rod is a coaxial push rod 47 which is axially displaceable therein, with its inner end shown lying against a seal ring 48 set in the piston, while its other, externally projecting end carries an impact plate 49. The latter, in its position illustrated in FIG. 3 forms with the radial widening 50 of the piston 45 next to the plate 49, a narrow annular qap open at its periphery. At its free end beyond the impact plate 49, the push rod 47 has an adjustable pressure plate 51 which is in operative abutting contact with the pivoted lever 52. The other end of this lever rolls on the top of the variable volume container 8 or, in the case of a compressed air breath protection device, on a corresponding membrane which is connected to an inhaling valve.

In the other pressure chamber 42 of the cylinder is located the connection 53 for the supply of pressurized gas and the inlet valve 54 related thereto. The inlet valve 54, along with its extension 55 provided on its center is mounted displaceably in the chamber 42 and has a seal ring 56 on its end face that faces the partition wall 44. A compression spring 57 presses the valve body 54 in the direction of its closed position.

Operation is as follows. In the position shown in FIG. 3 the pressure in the supply line 53 is imparted to the pressure chamber 41. Since the seal ring 56 has a larger diameter than the seal ring 48, the push rod 47 remains in abutment on the seal ring 48 as shown in the drawing, and the piston 45 exerts a pressino force through the lever 52 against the variable volume container or the membrane 8, so that the apparatus functions in over-pressure operation. With every drawing of breath the piston 45 makes a stroke movement alonq with the lever 52 in accordance with the translation ratio of the lever.

In the pressure chamber 42 the over-pressure holds the inlet valve 54 in its left stop position shown in the drawing. The force of the spring 57 is so designed that it is somewhat less than the force which is produced from the pressure and the surface at the seal 58, where the extension 55 of the valve body passes through the cylinder wall.

If in consequence of a major leakage the part 8, hereafter designated as the breathing bellows, is pressed together additionally to a certain extent, the piston 45 then comes into abutment on the right-hand inner wall of the pressure chamber 41 and moves the push rod 47 away from the seal 48. This condition is shown in FIG. 4. Since gas can flow around the outer side of the push rod, the pressure chambers 41 and 42 are emptied and the spring 57 displaces the inlet valve 54 to the right into its closed position (compare FIG. 4). Not so much air or oxygen can flow through the nozzle provided in the pressure gas supply 53 as flows out of the opening made free at the seal ring 48. In consequence the chamber 41 loses pressure, which means that the protective breathing device can now be operated without over-pressure by breathing.

Only when the breathing bellows 8 is filled to capacity, for example by actuation of the flushing valve, so that it shifts the push rod 47 with the hollow piston 45 to its left extreme position, does the piston 45 bear against the extension 55 and displace the inlet valve 54 to the left. The device then again functions in over-pressure operation.

In order to adjust precisely the reestablishment of over-pressure the extension 55 passing through the valve 54 is adjustable. A screw stud or some other type of axial guide is used to prevent twisting of the inlet valve 54 in the course of this adjustment.

The impact plate 49 has the function of performing the emptying of the pressure chamber 41 as fast as possible when the piston 45 comes into abutment with the right-hand cylinder wall. In that way the gas flowing out impinges on a greater surface and provides for an amplified lifting off of the push rod 47 from the seal ring 48.

FIGS. 5 and 6 show a similar cylinder and piston unit. For better understanding, corresponding parts are again provided with the same reference numerals.

The cylinder 40 is subdivided into two pressure chambers 41 and 42 as in the previously described example, with the piston and the outlet valve in the chamber 41 and the inlet valve in the pressure chamber 42. In contrast to the previous example, the outlet valve 60 in this case is not inside the piston but is disposed separately in the cylinder wall, while the piston 61 is a solid single piece. Furthermore, the inlet valve 54 is connected with a pull-knob 62.

The pull-knob 62 has a stop surface 62a for arresting a swinging lever 63 when the latter is located in the position shown in FIG. 5. In this case the outlet valve 60 is held in its closed position by the over-pressure prevailing in the pressure chamber 41. At its free end the lever 63 has a pressure plate 64 which is adjustable relative to the lever 63. This pressure plate 64 is so positioned that in the case of normal stroke movements of the breath bellows 8 and consequently of the piston 61, it is not touched. If however an abnormally high loss of gas occurs, so that the breath bellows 8 sinks heavily downwards, the piston 61 bumps against the pressure plate 64 and pushes it somewhat. The opposite end of the pivoted lever 63 is thereby moved downwards. In consequence the stop at the surface 62a of the pull-knob 62 is removed and the outlet valve 60 is opened at the same time. The pressure prevailing in the chamber 41 sinks rapidly and the inlet valve 54, as in the case of the previous example goes into its closed position. This is the condition shown in FIG. 6.

If and when the leakage is eliminated, the breath bellows 8 again takes up its normal stroke position. In consequence the piston 61 is again displaced so far into the chamber 41 that it runs against the extension of the inlet valve 54 and opens the latter. The pressure chamber 41 is then filled with over-pressure and the piston 61 exerts the necessary force on the breath bellows 8 for over-pressure operation of the system. Upon opening of the inlet valve 54 the pivoted lever 63 automatically snaps into its blocking position against the surface 62a as the result of the spring 65 acting on it.

Because the inlet valve 54 is connected with the pull-knob 62, the latter also enables over-pressure operation to be established manually.

It is finally to be noted that in FIG. 5 there is shown the application of the cylinder and piston unit of the invention in a compressed air breathing aid device, of which the inhaling valve 66 is built into the pressurized gas line 67 so that it closes under the force of the supply pressure. This valve is operatively connected with the breath bellows 8 in a manner already known, for example by the basculating lever 68 shown in the drawing. With this arrangement there is offered the possibility of connecting the protective breathing aid device and the cylinder and piston unit directly to high pressure, thus dispensing with a pressure reducer. The forces then automatically equalize each other at the bellows 8.

The embodiments according to FIGS. 3 to 6 are distinguished by the fact that in the case of major leakage the system is automatically switched over to under-pressure operation and that with complete filling of the breath bellows 8 over-pressure operation is automatically reestablished. At the same time, it is assured by the geometry of the swinging lever 52 that the over-pressure slightly increases with inhaling and slightly decreases with exhaling.

The cylinder and piston unit in either form according to FIGS. 3 to 6 is also suited for replacing the simple cylinder and piston unit illustrated in FIG. 2, whereby there also over-pressure regulation is automatically turned off at an adjustable lower stroke limit of the breath bellows, while the apparatus nevertheless remains capable of entertaining breathing in normal operation and the overpressure is automatically reestablished when an adjustable upper stoke limit is reached.

Although the invention has been described with reference to particular illustrative example, the above description shows that features of one embodiment have considerable applicability to other embodiments and that a range of variations and modifications are possible within the inventive concept.

I claim:

1. Protective breathing aid device suitable for operation under an overpressure during both inhalation and exhalation phases, comprising an exhaling duct, a $CO_2$-absorber, an equalization gas-containing chamber of variable volume having a movable wall and an inhaling duct, connected in sequence to provide a gas circulating path from said exhaling duct through said $CO_2$-absorber and said chamber of variable volume to said inhaling duct, means for subjecting said chamber of variable volume to a force tending to reduce the volume of said chamber and of a magnitude for producing a sufficient pressure rise in said chamber for establishment of a desired overpressure of gas in said circulation path, a compressed gas supply reservoir of gas supplying oxygen for breathing and means including at least one duct line for leading gas from said supply reservoir to said inhaling duct, said means for subjecting said chamber to said force comprising:

a cylinder-and-piston unit (13, 26, 40, 45, 61) including a cylinder and a piston therein, means for continuously supplying gas from said compressed gas supply reservoir to said cylinder during both inhalation and exhalation phases and mechanical means for enabling said piston to exert force continuously against said movable wall of said variable volume chamber and thereby to produce a continuous desired overpressure in said chamber.

2. Protective breathing aid device according to claim 1 in which said mechanical means comprise a pivoted lever (52) for transferring force from the piston of said piston-and-cylinder unit to said movable wall of said variable volume chamber, said lever having lever arm dimensions and angles of force-application such as to cause the force exerted against said movable wall of said variable volume chamber (8) to increase with the emptying of said chamber and to decrease with the filling thereof.

3. Apparatus according to claim 1 in which said cylinder-and-piston unit (40, 45, 61) is equipped with an outlet valve (47, 60) constituted so as to open when the piston (45, 61) of said cylinder-and-piston unit moves beyond a predetermined stroke position thereof for diminution of pressure on the piston, said piston being further equipped for blocking the further supply of compressed gas to said cylinder-and-piston unit in response to said diminution of pressure.

4. Protective breathing aid device according to claim 3, in which said cylinder-and-piston unit is equipped with an inlet valve (54) for supply of compressed gas to the cylinder thereof, said inlet valve being constituted so as to be affected by the pressure acting on the piston of said unit in the opening sense and being affected in the closing sense by the pressure of said compressed gas supplied to the valve.

5. Protective breathing aid device according to claim 4, in which the cylinder of said cylinder-and-piston unit comprises a first (41) and a second (42) pressure chamber, said piston (45, 61) and said outlet valve (47, 60) being located in said first chamber (41) and said inlet valve (54) being located in said second chamber (42), and a partition (44) having a central valve opening (43) for said inlet valve to be opened or closed by operation of said inlet valve.

6. Protective breathing aid device according to claim 5, in which said inlet valve (54) has a movable piece having an extension (55) passing through said valve opening (43) in said partition for automatic establishment of said desired overpressure.

7. Protective breathing aid device according to claim 4, in which said inlet valve (54) is equipped with an interlock (63) for blocking said inlet valve in its open position, said interlock having a configuration whereby it is released by the piston rod (61) of said cylinder-and-piston unit when its stroke position goes beyond a predetermined position, for automatically shutting off pressurized operation of the device.

8. Protective breathing aid device according to claim 7, in which said interlock (63) is of a configuration and disposition by which said outlet valve (60) of said cylinder-and-piston unit is opened when said interlock is released from its position in which it blocks said inlet valve in the open position of the latter.

9. Protective breathing aid device according to claim 4, in which said inlet valve (54) is of a configuration for maintaining the effective pressure surfaces in its open position.

10. Protective breathing aid device according to claim 4, in which the piston (45) of said cylinder-and-piston unit is hollow and in which said outlet valve is constituted as a push-rod (47) axially shiftable inside said piston (45) and a valve seat (48) is provided in the piston bore for cooperation with said push-rod (47), gas being able to flow around said push-rod (47) when it is off said valve seat (28) and a radially extending impact plate (49) being provided at the extremity of said push-rod remote from said valve seat forming a narrow flat annular gap with the corresponding end (50) of said piston when said push-rod is seated on said valve seat, whereby when said push-rod moves off said valve seat, gas passing around it will impinge on said impact plate.

11. Protective breathing aid device of the compressed air type for operation under an overpressure during both inhalation and exhalation phases having an exhaling duct, a $CO_2$-absorber, an inhaling duct and a bellows chamber having a movable wall (8) connected together so as to provide a gas circulation path leading from said exhaling duct, passing through said $CO_2$-abosorber and then through said bellows chamber, to said inhaling duct, a source of compressed air, valve means responsive to movement of said movable wall for connecting said source to said gas circulation path and means actuated by a said movable wall under collapsing movement of said bellows chamber for operating said valve means for admission of compressed air to said circulating path, said device incorporating the improvement comprising:

a cylinder-and-piston unit (13, 41, 42, 61, . . . ) having a piston and a cylinder in which said piston is displaceable, means for continuously supplying compressed air from said source to said cylinder during both inhalation and exhalation phases, said piston being mechanically connected to and thereby bearing against said movable wall for subjecting said movable wall to a pressure from said source in a sense tending to move said movable wall in the direction for opening said valve means for admitting compressed air to said circulation path, and thereby providing a continuous desired overpressure in said path.

12. Protective breathing aid device according to claim 11, in which said valve means is connected to said circulation path in said bellows chamber.

* * * * *